(12) United States Patent
Jee et al.

(10) Patent No.: US 10,890,549 B2
(45) Date of Patent: Jan. 12, 2021

(54) WEARABLE SENSOR AND METHOD FOR MANUFACTURING SAME

(71) Applicant: MCELL CO., LTD., Seongnam-si (KR)

(72) Inventors: Seung Hyun Jee, Seoul (KR); Sun Hee Kim, Seoul (KR)

(73) Assignee: MCELL CO., LTD.

( * ) Notice: Subject to any disclaimer, the term of this patent is extended or adjusted under 35 U.S.C. 154(b) by 196 days.

(21) Appl. No.: 16/081,875

(22) PCT Filed: Dec. 9, 2016

(86) PCT No.: PCT/KR2016/014423
§ 371 (c)(1),
(2) Date: Aug. 31, 2018

(87) PCT Pub. No.: WO2017/150789
PCT Pub. Date: Sep. 8, 2017

(65) Prior Publication Data
US 2019/0094168 A1  Mar. 28, 2019

(30) Foreign Application Priority Data

Mar. 2, 2016  (KR) .................. 10-2016-0025334

(51) Int. Cl.
*A61B 5/11* (2006.01)
*G01N 27/12* (2006.01)
(Continued)

(52) U.S. Cl.
CPC ............. *G01N 27/12* (2013.01); *A61B 5/11* (2013.01); *A61B 5/6804* (2013.01);
(Continued)

(58) Field of Classification Search
CPC .... G01N 33/36; G01N 27/127; G01N 33/497; A61B 5/11; A61B 5/6804;
(Continued)

(56) References Cited

U.S. PATENT DOCUMENTS

2017/0027473 A1* 2/2017 Lai .................. A61B 5/7278
2017/0060298 A1* 3/2017 Hwang .............. G06F 1/163

FOREIGN PATENT DOCUMENTS

KR 20110057267 A 5/2011
KR 101560595 B1 10/2015
(Continued)

OTHER PUBLICATIONS

Written Opinion for PCT/KR2016/014423 dated Sep. 13, 2018.
(Continued)

*Primary Examiner* — Robert R Raevis
(74) *Attorney, Agent, or Firm* — Renaissance IP Law Group LLP

(57) ABSTRACT

The present invention provides a wearable sensor including a fiber; a self-assembled monolayer formed on at least one surface of the fiber and including a functional group; a carbon nanotube layer formed on the self-assembled monolayer by adsorbing a plurality of carbon nanotubes on the self-assembled monolayer; and an electrode electrically connected to the carbon nanotube layer.

12 Claims, 5 Drawing Sheets

(51) Int. Cl.
*G01N 33/36* (2006.01)
*A61B 5/00* (2006.01)
*G01N 33/497* (2006.01)
*A61B 5/113* (2006.01)
*A61B 5/04* (2006.01)

(52) U.S. Cl.
CPC ............ *G01N 27/127* (2013.01); *G01N 33/36* (2013.01); *A61B 5/04* (2013.01); *A61B 5/113* (2013.01); *A61B 2562/0285* (2013.01); *A61B 2562/12* (2013.01); *G01N 33/497* (2013.01)

(58) Field of Classification Search
CPC ........ A61B 2562/12; A61B 2562/0285; A61B 5/113; A61B 5/04
USPC ........ 73/335.03, 763, 768, 774–776, 862.68, 73/159; 338/13, 2, 47; 977/902, 932, 977/953, 961, 840–901
See application file for complete search history.

(56) References Cited

FOREIGN PATENT DOCUMENTS

KR  20150110414 A  10/2015
KR  20160019570 A   2/2016

OTHER PUBLICATIONS

International Search Report for PCT/KR2016/014423 dated Mar. 29, 2017.

Kim, Sun Hee, "A design of the smart clothing for respiration monitoring using the conductive fabrics coated with the non-metal materials", Creative Commons, Dissertation, Jul. 2015, p. 1-158, Yonsei University, Seoul, Republic of Korea.

Luo, Ji et al., "A Silver Nanoparticle-Modified Evanescent Field Optical Fiber Sensor for Methylene Blue Detection", Sensors, Mar. 21, 2013, p. 3987-3997, vol. 13.

\* cited by examiner (a)

(b)

(c)

(a)        (b)

(c)

(a)

(b)

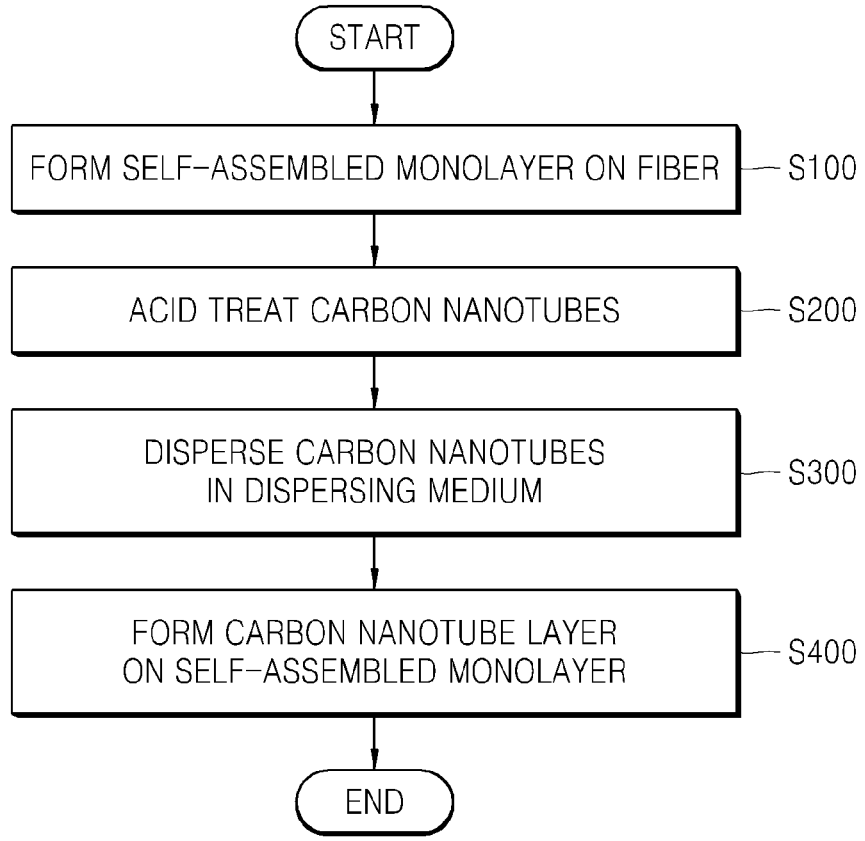
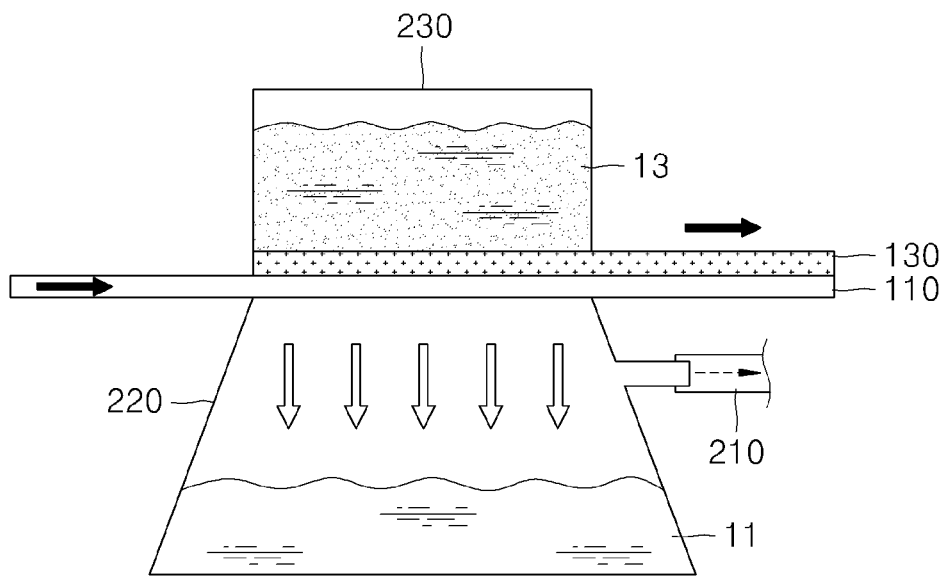

US 10,890,549 B2

WEARABLE SENSOR AND METHOD FOR MANUFACTURING SAME

TECHNICAL FIELD

The present invention relates to a wearable sensor and a method for manufacturing same, and more particularly, to a wearable sensor that senses the resistance displacement of a carbon nanotube layer according to the deformation of a fiber, and a method for manufacturing same.

BACKGROUND ART

Recently, due to the development in medical technology, desires on the promotion of health increase and concerns about information and communication technologies (ICT) increase, and thus, various wearable health care apparatuses and systems using the internet of things are appearing.

The conventional wearable devices are mere smart devices which could be worn on the specific parts of the body such as a watch and a wristlet. Accordingly, the securing of the sensitivity of a sensor for effectively sensing the biotransformation is limited. In addition, the conventional wearable devices are worn around the body apart from clothes, and wearing is inconvenient and a user may feel a pressure around a wearing part during wearing.

Therefore, works achieving a wearable apparatus by directly coating a sensor on a clothe material such as a fiber are required for ordinary wearing and for improving the sensitivity of the sensor. However, a fibrous apparatus (or sensor) which is a true wearable apparatus is not supplied so far.

(Patent Document 1) Korean Laid-open Patent Publication No. 10-2015-0110414

DISCLOSURE

Technical Problem

The present invention provides a wearable sensor of which wearability is excellent without stuffiness and inconvenience by forming a carbon nanotube layer on a fiber, and a method for manufacturing same.

Technical Solution

A wearable sensor according to an embodiment of the present invention includes a fiber; a self-assembled monolayer including a functional group and being formed on at least one surface of the fiber; a carbon nanotube layer formed on the self-assembled monolayer by adsorbing a plurality of carbon nanotubes on the self-assembled monolayer; and an electrode electrically connected to the carbon nanotube layer.

A ductile protective layer which is coated on the carbon nanotube layer may be further included.

The self-assembled monolayer may include a root unit combined with the surface of the fiber; and a functional group unit including the functional group and being connected with the root unit.

The functional group may be at least one selected from the group consisting of an amine group (—NH), an amino group (—NH$_2$), a thiol group (—SH), a carboxyl group (—COOH), a formyl group (—CHO), a cyanato group (—OCN), a silanol group (Si—OH), a phosphine group (—PO$_2$H$_2$), a phosphone group (—PO$_3$H$_2$), a sulfone group (—SO$_3$H), and an epoxy group.

A hydroxyl group (—OH) may be formed on the surface of the carbon nanotube, and the hydroxyl group (—OH) of the carbon nanotube and the functional group of the self-assembled monolayer may make an ionic bond.

The fiber may be formed using an elastic material.

The resistance displacement of the carbon nanotube layer according to the deformation of the fiber may be sensed.

A method for manufacturing a wearable sensor according to another embodiment of the present invention includes forming a self-assembled monolayer including a functional group on a fiber; acid treating carbon nanotubes; dispersing the carbon nanotubes in a dispersing medium; and forming a carbon nanotube layer on the self-assembled monolayer by providing on one surface of the fiber a dispersion solution in which the carbon nanotubes are dispersed in the dispersing medium.

The carbon nanotubes may be vacuum-adsorbed on the self-assembled monolayer while filtering the dispersion solution, by forming a vacuum pressure on the other surface of the fiber, in the forming the carbon nanotube layer.

The fiber may be immersed in a surface treatment solution including the functional group, for forming the self-assembled monolayer on the at least one surface of the fiber, in the forming the self-assembled monolayer.

A step of forming a ductile protective layer which is coated on the carbon nanotube layer, may be further included.

The carbon nanotube layer may be continuously formed on the self-assembled monolayer while transporting the fiber in a crossing direction to the providing direction of the dispersion solution, in the forming the carbon nanotube layer.

At least a portion of carbon bonds may be removed from the surface of the carbon nanotubes during acid treating the carbon nanotubes, in the acid treating the carbon nanotubes, and a step of forming a hydroxyl group (—OH) on the surface of the carbon nanotube from which the carbon bond is removed, may be further included.

The functional group of the self-assembled monolayer and the hydroxyl group (—OH) of the carbon nanotube may make an ionic bond, in the forming the carbon nanotube layer.

Advantageous Effects

The wearable sensor according to an embodiment of the present invention provides carbon nanotubes (CNT) on a fiber to form a carbon nanotube layer, and the resistance displacement of the carbon nanotube layer according to the deformation of the fiber may be sensed or measured. Accordingly, the deformation of the fiber may be sensed by the resistance displacement of the carbon nanotube layer, the biotransformation of a wearer may be sensed by measuring the resistance displacement due to the deformation of the fiber, which may be displaced according to the biotransformation of the wearer.

In addition, in the present invention, a self-assembled monolayer including a functional group is formed on a fiber, a hydroxyl group (—OH) is formed on the surface of carbon nanotube, and a carbon nanotube layer is formed on the self-assembled monolayer formed in the fiber, and the bonding force between the fiber and the carbon nanotube layer may be increased due to the ionic bond of the functional group and the hydroxyl group, and thus, the sensitivity and durability of the wearable sensor may be improved. In addition, a ductile protective layer is coated on the carbon nanotube layer to prevent the exfoliation of the carbon nanotube layer.

Meanwhile, in the method for manufacturing a wearable sensor of the present invention, a carbon nanotube layer is formed by vacuum adsorption, and the carbon nanotube layer is adsorbed well on the fiber and a processing time for forming the carbon nanotube layer may be decreased. In addition, since the carbon nanotube layer is formed by an in-line process while transporting the fiber, the mass production of the wearable sensor may be further improved.

BRIEF DESCRIPTION OF THE DRAWINGS

FIG. 5 is a flowchart showing a method for manufacturing a wearable sensor according to another embodiment of the present invention.

FIG. 6 is a schematic cross-sectional view showing the manufacturing process of a wearable sensor according to another embodiment of the present invention.

MODE FOR CARRYING OUT THE INVENTION

Figure 1:
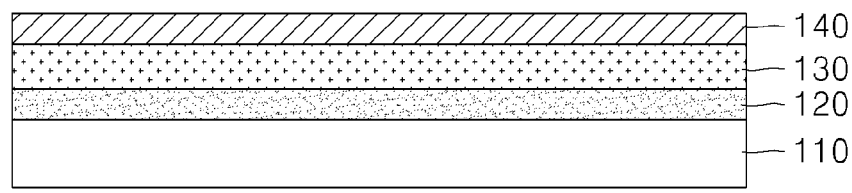
FIG. 1 is a schematic cross-sectional view showing a wearable sensor according to an embodiment of the present invention.

Hereinafter, embodiments of the present invention will be described in detail with reference to the accompanying drawings. The present invention may, however, be embodied in different forms and should not be construed as limited to the embodiments set forth herein. Rather, these embodiments are provided so that this disclosure will be thorough and complete, and will fully convey the scope of the present invention to those skilled in the art. In the explanation, the same element is imparted with the same reference numeral, and the dimensions of elements may be partially exaggerated for clarity of illustration. Like reference numerals refer to like elements throughout.

FIG. 1 is a schematic cross-sectional view showing a wearable sensor according to an embodiment of the present invention.

Referring to FIG. 1, the wearable sensor according to an embodiment of the present invention may include a fiber (110); a self-assembled monolayer (120) which is formed on at least one surface of the fiber (110) and includes a functional group; a carbon nanotube layer (130) formed on the self-assembled monolayer (120) by adsorbing a plurality of carbon nanotubes (131) on the self-assembled monolayer (120); and an electrode (not shown) which is electrically connected with the carbon nanotube layer (130).

The fiber (110) may be a material of clothing which is wearable on the human body, and may be a synthetic fiber, etc. In addition, the fiber (110) may be used in a wearable device and has a grain with different properties for each fiber (110). In this case, the fiber (110) shows different displacement amount of resistance with respect to an elongated length according to the grain, and directional property may be imparted with the resistance displacement of the carbon nanotube layer (130). In addition, since there are openings between the fibers (110), the carbon nanotubes (131) may remain on the surface of the fiber (110) and only a dispersion medium may penetrate between the fibers (110). Accordingly, if the fiber (110) is used, a vacuum adsorption method may be used for forming the carbon nanotube layer (130). The vacuum adsorption method will be described in detail below.

A self-assembled monolayer (SAM, 120) may include a functional group, and may be formed on at least one surface of the fiber (110). If the self-assembled monolayer (120) is formed on the surface of the fiber (110) and the surface of the fiber (110) is treated, the bonding force between the fiber (110) and the carbon nanotube layer (130) is increased to form the carbon nanotube layer (130) well on the fiber (110).

The carbon nanotube layer (130) may be formed on the self-assembled monolayer (120) by the adsorption of a plurality of carbon nanotubes (CNT, 131) on the self-assembled monolayer (120). In addition, the resistance of the carbon nanotube layer (130) may be displaced according to the change of the surface area thereof or the change of the number of the contact points of the plurality of carbon nanotubes (131). Accordingly, the resistance of the carbon nanotube layer (130) may be displaced according to the deformation of the fiber (110), and sensing may be performed using the resistance displacement of the carbon nanotube layer (130). A wearable sensor using the carbon nanotubes (131) that may analyze the movement of the body through the resistance displacement with high sensitivity during the deformation of the length and area of the fiber (110), may be provided. In addition, a wearable sensor in which the carbon nanotube layer (130) is formed on the fiber (110) and thus, achieving excellent wearing property without stuffiness and inconvenience, may be provided.

The electrode (not shown) may be electrically connected with the carbon nanotube layer (130), and may be formed at both ends of the carbon nanotube layer (130). By flowing current through the carbon nanotube layer (130) via the electrode (not shown), the resistance displacement of the carbon nanotube layer (130) may be sensed.

Meanwhile, the electrode (not shown) may be formed by sewing conductive threads such as silver (Ag) threads and gold (Au) threads. In this case, current may be uniformly supplied to the entire carbon nanotube layer (130) without short circuit and the electrode may be simply manufactured, as well as the current may be supplied to entire carbon nanotube layer (130) without short. In addition, the electrode may be formed without a separate etching process after forming a protective layer (140). In addition, if the fiber (110) and the carbon nanotube layer (130) are sewn using conductive threads, the electrode may be simply manufactured, and in addition, the fiber (110) and the carbon nanotube layer (130) may be firmly bonded (or fixed).

The fiber (110) may be formed using an elastic material. In order to sense the biotransformation (for example, breathing) of a man, the resistance of the carbon nanotube layer (130) is required to displace according to the biomechanical movement of a wearer. In this case, if the fiber (1100 is formed using an elastic material, the fiber (110) may be deformed according to the biomechanical movement of a wearer, and the resistance of the carbon nanotube layer (130) may be displaced according to the deformation of the fiber (110). Thus, by measuring the resistance displacement of the carbon nanotube layer (130) according to the biomechanical movement of a wearer, the biotransformation of the wearer may be sensed.

The wearable sensor of the present invention may further include a ductile protective layer (140) coated on the carbon nanotube layer (130). The protective layer (140) may be formed using a soft material and may be coated on the carbon nanotube layer (130). The carbon nanotube layer (130) may be exfoliated due to the excessive deformation (for example, frequent deformation, the deformation greater than the elasticity limitation of the carbon nanotube layer, etc.) or the rapid deformation of the fiber (110). However, in the present invention, by the ductile protective layer (140) which may be retractile according to the deformation of the fiber (110), the exfoliation of the carbon nanotube layer (130) may be prevented, and the stress of the carbon nanotube layer (130) due to the surface change according to the deformation of the fiber (110) may be relieved. The protective layer (140) may be formed using a resin, and any soft material having excellent elasticity to be retractile according to the deformation of the fiber (110), may be satisfied, without specific limitation.

Figure 2:
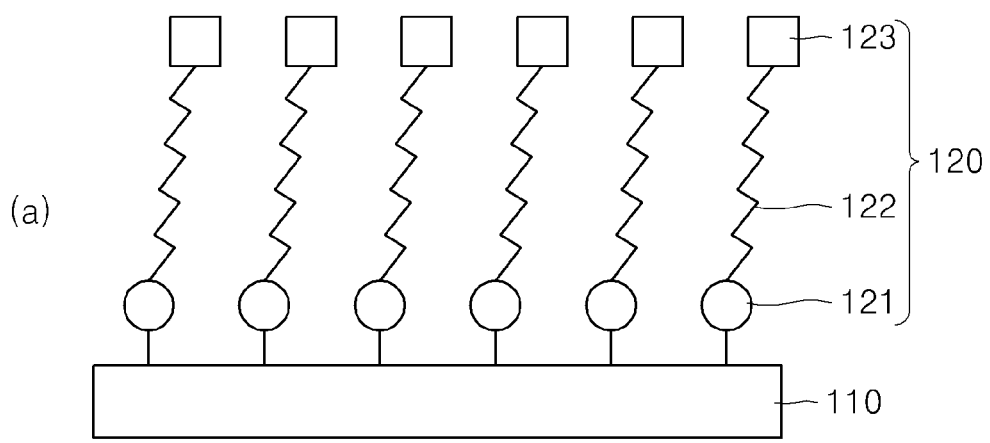
FIG. 2 is a conceptual diagram for explaining the bonding of a self-assembled monolayer and a carbon nanotube layer according to an embodiment of the present invention.
Figure 2:
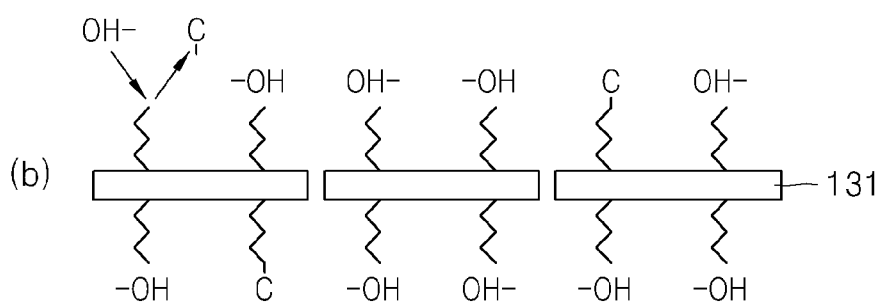
Figure 2:
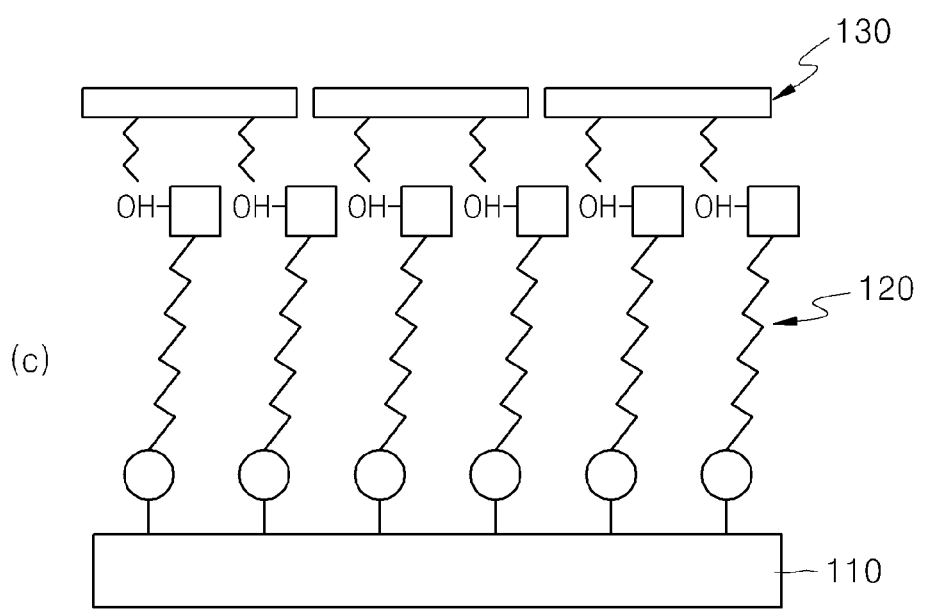

FIG. 2 is a conceptual diagram for explaining the bonding of a self-assembled monolayer and a carbon nanotube layer according to an embodiment of the present invention, wherein (a) of FIG. 2 is a conceptual diagram of a self-assembled monolayer formed on a fiber, (b) of FIG. 2 is a conceptual diagram showing the formation of a hydroxyl group on the surface of the carbon nanotube, and (c) of FIG. 2 is a conceptual diagram showing the bonding of a self-assembled monolayer and a carbon nanotube layer.

Referring to FIG. 2, the self-assembled monolayer (120) includes a root unit (121) combined with the surface of the fiber (110); and a functional group unit (123) which includes the functional group and is connected with the root unit (121). The root unit (121) may be combined with the surface of the fiber (110) and may be selected according to the kind of the fiber (110). In this case, generally, the root unit (121) may be selected from materials including a silicon atom (Si) (for example, silane-based material).

The functional group unit (123) may include the functional group which may impart functionality and may be connected with the root unit (121). In this case, the functional group unit (123) may be selected from diverse functional groups according to a part to be reacted later (that is, according to a material to be attached).

In addition, the self-assembled monolayer (120) may further include a backbone (122) connecting the root unit (121) and the functional group unit (123). The backbone (122) may be mainly composed of alkyl chains, and may be hydrocarbon chains or fluoro-carbon chains.

The functional group may be at least one selected from an amine group (—NH), an amino group (—$NH_2$), a thiol group (—SH), a carboxyl group (—COOH), a formyl group (—CHO), a cyanato group (—OCN), a silanol group (Si—OH), a phosphine group (—$PO_2H_2$), a phosphone group (—$PO_3H_2$), a sulfone group (—$SO_3H$), and an epoxy group. Through the functional group, the surface of the fiber (110) is charged with (+) to impart the surface of the fiber (110) with an electrostatic force. If a hydroxyl group (—OH) is formed on the surface of the carbon nanotube (131), the functional group and the hydroxyl group may make an ionic bond. Accordingly, the bonding force between the fiber (110) and the carbon nanotube layer (130) (that is, the bonding force between the self-assembled monolayer and the carbon nanotube layer) may be improved.

In case where the self-assembled monolayer (120) is formed on the fiber (110), a silane-based material may be selected as the root unit (121) to be bonded to the surface of the fiber (110). In this case, the surface treatment material (or solution) forming the self-assembled monolayer (120) may be a silane-based material (or solution) including at least one functional group selected from an amine group (—NH), an amino group (—$NH_2$), a thiol group (—SH), a carboxyl group (—COOH), a formyl group (—CHO), a cyanato group (—OCN), a silanol group (Si—OH), a phosphine group (—$PO_2H_2$), a phosphone group (—$PO_3H_2$), a sulfone group (—$SO_3H$), and an epoxy group, and may be aminosilane, 3-aminopropyltriethoxysilane (APTES), etc. The silane-based material includes groups capable of connecting a polymer and an inorganic material at the same time, and may be bonded to the fiber (110) well. In this case, similar to a glass fiber, if the hydroxyl group (—OH) of the surface of a natural fiber is utilized, silicon (Si) included in the silane-based material makes an ionic bond with the hydroxyl group on the surface of the fiber (110) so that the root unit (121) may bonded to the surface of the fiber (110) well. Accordingly, in case of using a silane-based material as the surface treatment material, the root unit (121) may bonded to the surface of the fiber (110) well, and the self-assembled monolayer (120) may be formed on the fiber (110). In addition, if the silane-based material is used, the ions of the surface treatment material may be guided on the surface of the fiber (110) in a certain direction, and the surface of the fiber (110) may be charged to impart the surface of the fiber (110) with electrostatic force.

The fiber (110) may be a natural fiber composite material utilizing the hydroxyl group on the surface of a natural fiber, and a hydroxyl group may be formed on the surface of the fiber (110) by activating the surface of the fiber (110). For the favorable bonding of the root unit (121) to the surface of the fiber (110), a hydroxyl group may be formed on the surface of the fiber (110) to activate the surface of the fiber (110). In this case, the fiber (110) may be immersed in a RCA solution obtained by mixing ammonia water ($NH_4OH$), hydrogen peroxide ($H_2O_2$) and de-ionized water (DI, $H_2O$) in a ratio of 1:1:5 for 5 to 20 minutes, to form a hydroxyl group on the surface of the fiber (110), and induce the formation of the self-assembled monolayer (120) well. For example, the self-assembled monolayer (120) may be formed through the bonding of the hydroxyl group ($OH^-$) which is activated on the surface of the fiber (110) and the silicon ion ($Si^{4+}$) of the silane-based material. Meanwhile, by spraying the RCA solution, the hydroxyl group may be formed on the surface of the fiber (110), the hydroxyl group may be formed on the surface of the fiber (110) by diverse methods, and the surface of the fiber (110) may be activated by other various methods.

On the surface of the carbon nanotube (131), a hydroxyl group (—OH) may be formed. As shown in (b) of FIG. 2, at least a portion of carbon bonds may be broken at the surface of the carbon nanotube (131), and a hydroxyl group may be formed at the broken site of the carbon bonds. If the hydroxyl group is formed on the surface of the carbon nanotube (131), the hydroxyl group of the carbon nanotube (131) and the functional group of the self-assembled monolayer (120) may make an ionic bond so that the carbon nanotube layer (130) may be adsorbed on the fiber (110) well.

In addition, the hydroxyl group (—OH) of the carbon nanotube (131) and the functional group of the self-assembled monolayer (120) may make an ionic bond. As shown in (c) of FIG. 2, the hydroxyl group of the carbon nanotube (131) and the functional group of the functional group unit (123) may make an ionic bond to form a carbon nanotube layer (130). For example, the hydroxyl group ($OH^-$) formed on the surface of the carbon nanotube (131)

and the amine group (NH⁺) of the functional group unit (123) may make an ionic bond. Accordingly, the fiber (110) and the carbon nanotube layer (130) may be combined with even stronger energy, and thus, the bonding force between the fiber (110) and the carbon nanotube layer (130) may be increased, and the sensitivity and the durability of the wearable sensor may be increased.

Figure 3:
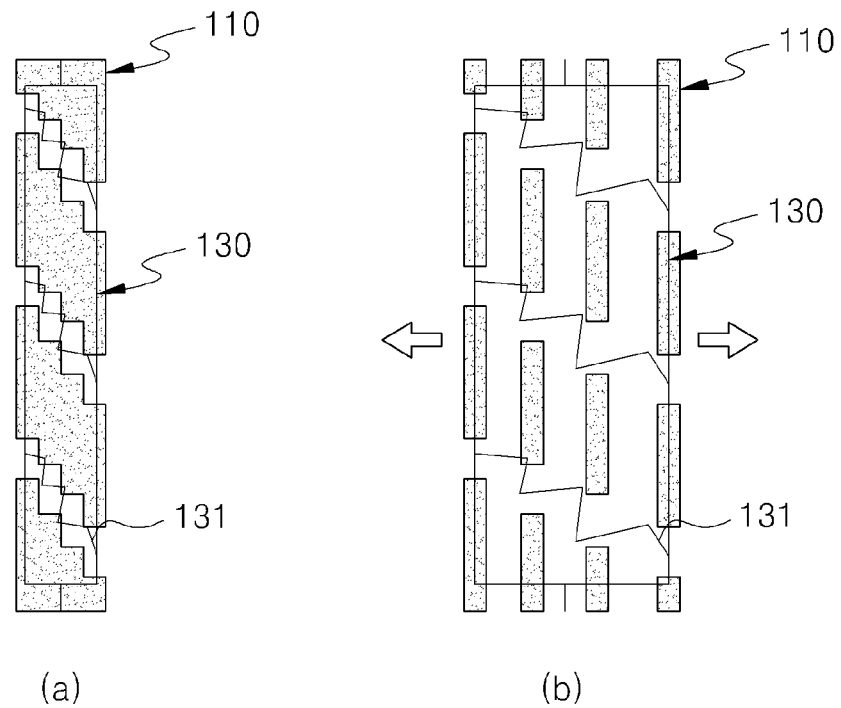
FIG. 3 is a diagram for explaining the resistance displacement of a carbon nanotube layer according to an embodiment of the present invention.
Figure 3:
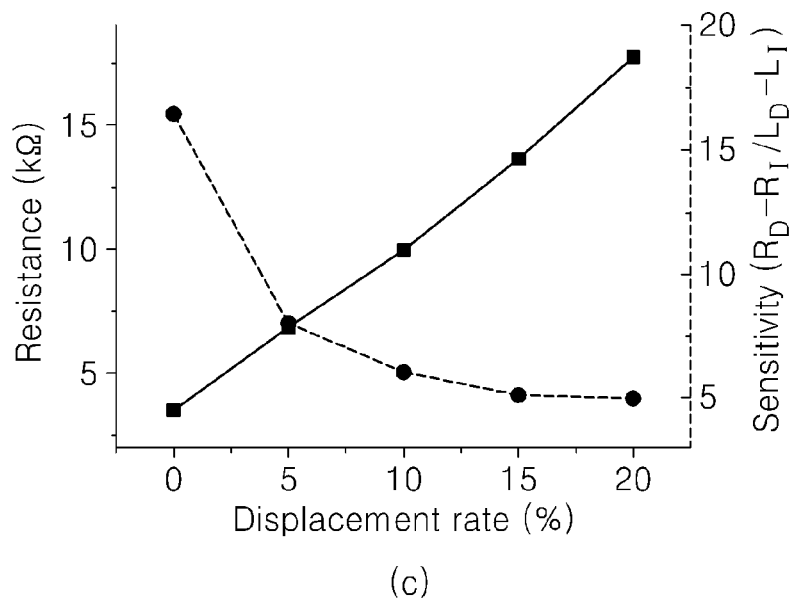

FIG. 3 is a diagram for explaining the resistance displacement of a carbon nanotube layer according to an embodiment of the present invention, wherein (a) of FIG. 3 corresponds to a diagram before the deformation of a fiber, (b) of FIG. 3 corresponds to a diagram after the deformation of a fiber, and (c) of FIG. 3 is a graph showing the resistance displacement and the sensitivity displacement according to the elongation of a fiber.

Referring to FIG. 3, the wearable sensor (110) of the present invention may sense or measure the resistance displacement of the carbon nanotube layer (130) due to the deformation of the fiber (110). As shown in (a) of FIG. 3, if the fiber (110) keeps a certain shape, the resistance of the carbon nanotube layer (130) may be kept constant. If the fiber (110) keeping the certain shape is deformed as shown in (b) of FIG. 3, the surface area of the carbon nanotube layer (130) or the contact point number of a plurality of carbon nanotubes (131) may change according to the deformation of the fiber (110) to displace the resistance of the carbon nanotube layer (130).

In the wearable sensor of the present invention, the resistance value of the carbon nanotube layer (130) may increase according to the increase of the fiber (110). The increase of the resistance value of the carbon nanotube layer (130) with the increase of the fiber (110) (that is, with the increase of the surface area of the carbon nanotube layer) may be confirmed in (c) of FIG. 3. That's because the length of the carbon nanotube (131) is increased, or the contact point number contacting the fiber (110) or the contact area of the carbon nanotube (131) is decreased. Meanwhile, since the elasticity limit of the carbon nanotube layer (130) is lower than that of the fiber (110), if elasticity approaches the elasticity limit due to the deformation of the fiber (110), the sensitivity may be degraded. Here, the sensitivity may be calculated according to an equation below.

$$\text{Sensitivity } (S) = R_D - R_I / L_D - L_I$$

($R_D$: resistance with length change, $R_I$: resistance without change of initial length, $L_D$: length with length change, and $L_I$: initial length)

In addition, in the wearable sensor of the present invention, since the resistance of the carbon nanotube layer (130) may be displaced according to the deformation of the fiber (110), sensing may be performed using the resistance displacement of the carbon nanotube layer (130). In case where the fiber (110) is formed using an elastic material, the fiber (110) may be deformed according to the biomechanical movement of a wearer, and the resistance of the carbon nanotube layer (130) may be displaced according to the deformation of the fiber (110). Through this, the biotransformation of a wearer may be sensed by measuring the resistance displacement of the carbon nanotube layer (130) according to the biomechanical movement of a wearer.

Figure 4:
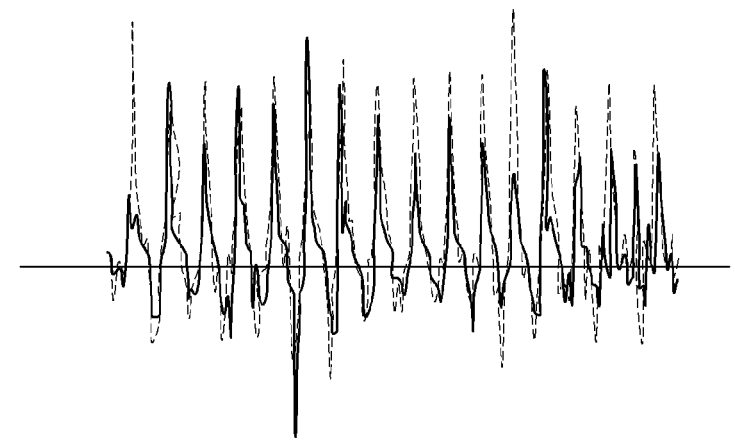
FIG. 4 is a comparison graph of wearable sensors according to an embodiment of the present invention and a comparative example.
Figure 4:
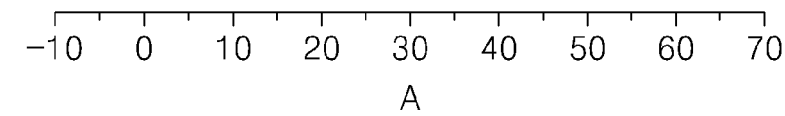
Figure 4:
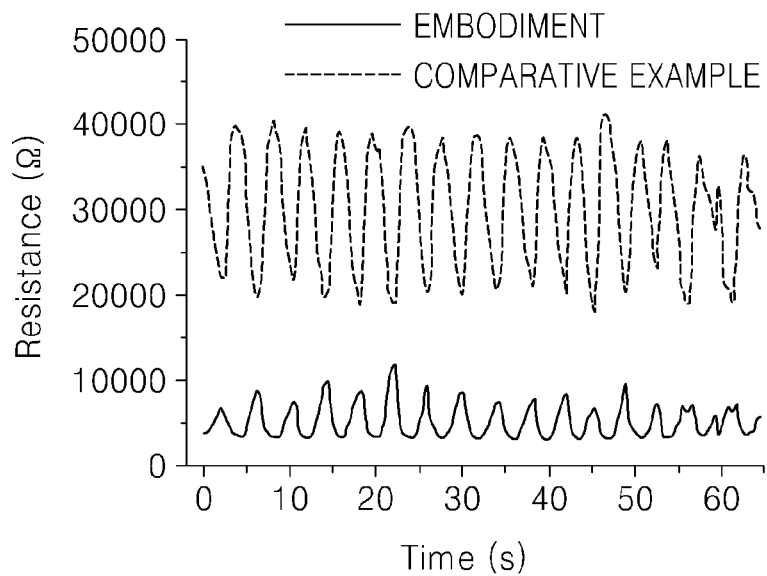

FIG. 4 is a comparison graph of wearable sensors according to an embodiment of the present invention and a comparative example, wherein (a) of FIG. 4 is a graph showing the respiration measurements of an embodiment of the present invention and a comparative example, and (b) of FIG. 4 is a graph showing the resistance value displacements of an embodiment of the present invention and a comparative example.

Table 1 shows the average resistance and sensitivity of an embodiment of the present invention and a comparative example during breathing for 60 seconds.

TABLE 1

| Breathing (60 seconds) | Average resistance (Ω) | Sensitivity |
|---|---|---|
| Embodiment (breath out) | 8404.74 | 2.54 |
| Embodiment (breath in) | 3308.36 | |
| Comparative Example (breath out) | 20242.66 | 1.803 |
| Comparative Example (breathe in) | 36500.19 | |

Referring to FIG. 4 and Table 1, the wearable sensor of the present invention may have a sensitivity of 2 to 2.7. The sensitivity of 2 or more would be better than the comparative example using a BioPAC sensor which is conventionally commonly used. Here, the BioPAC sensor is a sensor used for bio-signal measurement and a mostly used sensor by people in a medical engineering field. Through the wearable sensor of the present invention, a breathing sensor (or bio-signal measurement sensor) having excellent performance may be provided, and the biotransformation may be sensed more accurately.

Meanwhile, in (a) of FIG. 4, a slight time difference is generated between an embodiment of the present invention and the comparative example, and in Table 1, the high and low values of the average resistances during breath out and breath in show contrary results. The sensitivity of the sensor is irrelevant but it is judged that the results were obtained because the wearable sensor of the present invention was put on the abdominal and the BioPAC used as the comparative example was put on the chest.

FIG. 5 is a flowchart showing a method for manufacturing a wearable sensor according to another embodiment of the present invention.

The method for manufacturing a wearable sensor according to another embodiment of the present invention will be explained in more detail referring to FIG. 5, but overlapping parts with the explanation on the wearable sensor according to an embodiment of the present invention will be omitted.

The method for manufacturing a wearable sensor according to another embodiment of the present invention may include forming a self-assembled monolayer including a functional group on a fiber (110) (S100); acid treating carbon nanotubes (S200); dispersing the carbon nanotubes in a dispersing medium (11) (S300); and forming a carbon nanotube layer (130) on the self-assembled monolayer by providing on one surface of the fiber (110) a dispersion solution (13) in which the carbon nanotubes are dispersed in the dispersing medium (S400).

First, a self-assembled monolayer including a functional group is formed on a fiber (110) (S100). The self-assembled monolayer may include a rood group bonded to the surface of the fiber (110); a functional group unit including the functional group and connected with the root unit; and a backbone connecting the root unit and the functional group unit. The root unit may be combined with the surface of the fiber (110), and may be selected according to the kind of the fiber (110). Generally, a silane-based (Si—) group may be selected as the root unit. The backbone may be mainly composed of alkyl chains, and may be hydrocarbon chains or fluoro-carbon chains. Lastly, the function group unit may include the functional group which may impart functionality and may be connected with the root unit (121). In this case, the functional group unit may be selected among diverse functional groups according to a part to be reacted (that is according to a material to be attached).

If the self-assembled monolayer is formed on the surface of the fiber (110) for the surface treatment of the fiber (110), the bonding force between the fiber (110) and the carbon nanotube layer (130) may increase, and the carbon nanotube layer (130) may be favorably formed on the fiber (110).

In the forming step of the self-assembled monolayer (S100), the fiber (110) may be immersed in a surface treatment solution to form the self-assembled monolayer on at least one surface of the fiber (110). Here, the fiber (110) may be transported through a transporting part (not shown) such as a conveyor belt and may be immersed in the surface treatment solution. In this case, the transporting part (not shown) may be formed of a belt (not shown) contacting the fiber (110) and a rotating roller (not shown) for moving the belt. The surface treatment solution may further include a silane-based material as the root unit which is bonded to the surface of the fiber (110). Here, the surface treatment solution may be aminosilane, 3-aminopropyltriethoxysilane (APTES), etc. Since the silane-based material has groups capable of connecting a polymer and an inorganic material at the same time, bonding with the fiber (110) may be favorable. In this case, similar to a glass fiber, if the hydroxyl group (—OH) on the surface of a natural fiber is utilized, silicon (Si) included in a silane-based material makes an ionic bond with the hydroxyl group of the surface of the fiber (110), and the root unit may be bonded to the surface of the fiber (110) well. Accordingly, if a silane-based material is included in the surface treatment solution, the root unit may be bonded to the surface of the fiber (110) well, and by only immersing the fiber (110) in the surface treatment solution, the self-assembled monolayer may be formed on the fiber (110). In addition, if the surface treatment solution including a silane-based material is used, the ions of the surface treatment material may be guided on the surface of the fiber (110) in a certain direction, the surface of the fiber (110) may be charged, and the surface of the fiber (110) may be imparted with an electrostatic force.

Meanwhile, the surface treatment solution may include 1 to 10 wt % of a silane-based material including the functional group. If the concentration of the silane-based material including the functional group is less than 1 wt %, the amount of the ions of the root unit and the functional group is small, and the forming rate of the self-assembled monolayer (120) on the surface of the fiber (110) is significantly decreased, and overall manufacturing processes of a wearable sensor take a long time, and the mass production of the wearable sensor may be degraded. These issues may become more serious if the wearable sensor is manufactured by an in-line method, causing continuous retention in the forming step (S100) of the self-assembled monolayer (120). Thus, the advantages of an in-line process may not be achieved. On the contrary, if the concentration of the silane-based material including the functional group is greater than 10 wt %, the forming rate of the self-assembled monolayer (120) on the surface of the fiber (110) becomes too fast, and the control of the forming thickness of the self-assembled monolayer (120) may become difficult. If the concentration of the silane-based material including the functional group is greater than 10 wt %, the thickness of the self-assembled monolayer (120) may increase despite short times. Accordingly, the control of the thickness of the self-assembled monolayer (120) is difficult by controlling only time. However, if the concentration of the silane-based material including the functional group is 10 wt % or less, and if the concentration of the silane-based material including the functional group is kept constant, the thickness of the self-assembled monolayer (120) may be controlled according to time.

Also, the fiber (110) may be a natural fiber composite material utilizing the hydroxyl group on the surface of a natural fiber, and the hydroxyl group may be formed on the surface of the fiber (110) by activating the surface of the fiber (110). For the favorable bonding of the root unit (121) to the surface of the fiber (110), a hydroxyl group may be formed on the surface of the fiber (110) to activate the surface of the fiber (110). In this case, the fiber (110) may be immersed in a RCA solution obtained by mixing ammonia water ($NH_4OH$), hydrogen peroxide ($H_2O_2$) and de-ionized water (DI, $H_2O$) in a ratio of 1:1:5 for 5 to 20 minutes, to form a hydroxyl group on the surface of the fiber (110), and to induce the formation of the self-assembled monolayer well. For example, the self-assembled monolayer may be formed through the bonding of the hydroxyl group ($OH^-$) which is activated on the surface of the fiber (110) and the silicon ion ($Si^{4+}$) of the silane-based material. Here, by spraying the RCA solution, the hydroxyl group may be formed on the surface of the fiber (110), the hydroxyl group may be formed on the surface of the fiber (110) by diverse methods, and the surface of the fiber (110) may be activated by other various methods.

Then, the carbon nanotubes (CNT) are acid treated (S200). By acid treating the carbon nanotubes, the carbon nanotubes may be surface treated. By the acid treatment, dangling bonds may be formed on the surface of the carbon nanotubes and hydroxyl groups (—OH) may be formed on the surface of the carbon nanotubes.

The carbon nanotubes may be acid treated using nitric acid. For example, the carbon nanotubes (for example, 1 g) are injected in 99% nitric acid (for example, 150 ml) to perform acid treatment. In this case, the acid treatment may be performed by a dipping method, and the acid treatment may be performed while stirring at a temperature of 100 to 150° C. for 3 to 5 hours for the efficient surface treatment of the carbon nanotubes. After taking out from the nitric acid, a washing process of the carbon nanotubes may be performed using de-ionized (DI) water, etc. until the pH of the carbon nanotubes becomes 7 (or neutral). For example, the carbon nanotubes taken out from the nitric acid may be rinsed with de-ionized water 5 to 10 times.

Meanwhile, if the acid treatment is performed using hydrochloric acid, chloride ions ($Cl^-$) may react with the carbon ions ($C^{4+}$) at the broken sites of carbon bonds, to form chloride groups (—Cl) at the broken sites of the carbon bonds. Thus, dangling bonds may be formed on the surface of the carbon nanotubes.

In the acid treatment step (S200) of the carbon nanotubes, at least a portion of the carbon bonds may be removed from the surface of the carbon nanotubes. If the carbon nanotubes are acid treated, the carbon bonds may be broken via an oxidation process (or by energy or heat due to acid), and unsaturated bonds may be formed on the surface of the carbon nanotubes.

Also, the method for manufacturing the wearable sensor of the present invention may further include a forming step (S250) of a hydroxyl group (—OH) on the surface of the carbon nanotube, where the carbon bond is removed. A hydroxyl group may attach to the position where the carbon bond is removed from the surface of the carbon nanotube to form the hydroxyl group on the surface of the carbon nanotube. The hydroxyl group may be provided from moisture in the air, or provided from water used during the washing process of the acid treated carbon nanotube. In addition, if de-ionized water is used as the dispersing medium (11), the hydroxyl group may be provided from the dispersing medium (11). If the hydroxyl group is formed on the surface of the carbon nanotube, the hydroxyl group of the carbon nanotube and the functional group of the self-assembled monolayer make an ionic bond, and the carbon nanotube layer (130) may be adsorbed well on the fiber (10).

The functional group may be at least one selected from an amine group (—NH), an amino group (—NH$_2$), a thiol group (—SH), a carboxyl group (—COOH), a formyl group (—CHO), a cyanato group (—OCN), a silanol group (Si—OH), a phosphine group (—PO$_2$H$_2$), a phosphone group (—PO$_3$H$_2$), a sulfone group (—SO$_3$H), and an epoxy group. Through the functional group, the surface of the fiber (110) may be charged with (+) to impart the surface of the fiber (110) with an electrostatic force, and the functional group and the hydroxyl group may make an ionic bond. Accordingly, the bonding force between the fiber (110) and the carbon nanotube layer (130) (that is, the bonding force between the self-assembled monolayer and the carbon nanotube layer) may be increased.

Also, the hydroxyl group of the carbon nanotube may make an ionic bond with the functional group in the functional group unit to form the carbon nanotube layer (130). For example, the hydroxyl group (OH$^-$) formed on the surface of the carbon nanotube and the amine group (NH$^+$) of the functional group unit may make an ionic bond. Accordingly, the fiber (110) and the carbon nanotube layer (130) may be combined with even stronger energy, and thus, the bonding force between the fiber (110) and the carbon nanotube layer (130) may be increased, and the sensitivity and the durability of the wearable sensor may be improved.

The carbon nanotubes are dispersed in the dispersing medium (11) (S300). The carbon nanotubes may be uniformly dispersed in the dispersing medium (11), and the carbon nanotubes may be uniformly dispersed by putting them in the dispersing medium (11) and using a dispersion method by ultrasonic waves or a stirring method. Here, the carbon nanotubes with hydroxyl groups formed on the surface thereon may be dispersed, or the carbon nanotubes from which at least a portion of carbon bonds is removed from the surface thereof may be put in de-ionized water which is used as the dispersing medium (11) to form hydroxyl groups on the surface of the carbon nanotubes. In case of putting the carbon nanotubes from which at least a portion of carbon bonds is removed from the surface thereof in de-ionized water, attraction with water molecules may increase due to the dangling bonds on the surface of the carbon nanotubes, hydroxyl groups may be formed at the sites where the carbon bonds are removed to charge the surface of the carbon nanotube with (−), and the surface of the carbon nanotube may be imparted with electrostatic force. The dispersing medium (11) may be de-ionized (DI) water, but any liquid in which the carbon nanotubes are not dissolved and which does not influence the carbon nanotubes may be satisfied, without specific limitation.

For example, the carbon nanotubes (for example, 30 mg) may be put in de-ionized water (for example, 1 L) and a dispersing process may be performed while stirring for 18 to 30 hours.

When the surface of the carbon nanotube is charged with (−) by the hydroxyl group, the surface of the carbon nanotube may be imparted with electrostatic force. Thus, the carbon nanotubes may be uniformly dispersed in the dispersing medium (11) and a stable dispersion solution (130) may be obtained without generating the precipitation phenomenon of the carbon nanotubes or the agglomeration phenomenon of the carbon nanotubes. Accordingly, the wearable sensor of the present invention with improved uniformity and reliability of the carbon nanotube layer (130) on the fiber (110) may be manufactured.

The carbon nanotube layer (130) is formed on the self-assembled monolayer by supplying onto one surface of the fiber (110) a dispersion solution (13) in which the carbon nanotubes are dispersed in the dispersing medium (S400). If the dispersion solution (13) of the carbon nanotubes is supplied onto the one surface of the fiber (110) while flowing from one surface to the other surface of the fiber (110), the dispersing medium (11) passes through the fiber (110) and is drained down, and only the carbon nanotubes remain (or trapped by filtering) on the fiber (110). Here, the dispersion solution (13) of the carbon nanotube may be supplied through a dispersion solution supplying vessel (230). The carbon nanotubes thus remained on the fiber (110) are dried to form the carbon nanotube layer (130). The resistance of the carbon nanotube layer (130) may be displaced according to the change of the surface area thereof or the change of the contact point number of a plurality of the carbon nanotubes. Thus, the resistance of the carbon nanotube layer (130) may be displaced according to the deformation of the fiber (110), and sensing may be performed using the resistance displacement of the carbon nanotube layer (130).

Also, the hydroxyl group of the carbon nanotube and the functional group of the self-assembled monolayer may make an ionic bond, and the fiber (110) and the carbon nanotube layer (130) may be combined with even stronger energy, and thus, the bonding force between the fiber (110) and the carbon nanotube layer (130) may increase, and the sensitivity and the durability of the wearable sensor may be improved.

In the forming step of the carbon nanotube layer (S400), the carbon nanotubes may be vacuum-adsorbed on the self-assembled monolayer while filtering the dispersion solution (13), by forming a vacuum pressure on the other surface of the fiber (110), in the forming the carbon nanotube layer. A vacuum pressure may be formed at the other surface of the fiber (110), and the vacuum pressure may be formed at the other surface of the fiber (110) by forming vacuum in a vacuum vessel (220) via a vacuum exhausting apparatus (210) connected therewith. Through this, the carbon nanotubes may be vacuum adsorbed on the self-assembled monolayer. In this case, the carbon nanotubes remaining on the fiber (110) by the filtering of the dispersion solution (13) may be vacuum adsorbed on the self-assembled monolayer to form the carbon nanotube layer (130) on the self-assembled monolayer. In case where the carbon nanotube layer (130) is formed on the self-assembled monolayer by a vacuum adsorption method by which the carbon nanotubes are adsorbed in a direction from one surface to the other surface of the fiber (110) by forming a vacuum pressure at the other surface of the fiber (110), the carbon nanotubes may penetrate into the fiber (110) by adsorption energy by a strong vacuum pressure, and the carbon nanotube layer (130) may be effectively adsorbed on the fiber (110). Also, since the dispersing medium (11) may be drained off through the fiber (110) smoothly by the vacuum pressure when compared with a case where vacuum is not formed, the carbon nanotube layer (130) may be formed fast. Thus, a processing time for forming the carbon nanotube layer (130) may decrease, and since the vacuum pressure is uniformly formed on the surface of the fiber (110), a uniform carbon nanotube layer (130) may be formed.

Meanwhile, if the carbon nanotube layer (130) is formed by the vacuum adsorption method, carbon nanotubes may be generated together with the dispersing medium (11) going through the surface of the fiber (110) due to the vacuum pressure. Thus, a certain amount (for example, 1 L) of the dispersion solution (13) of the carbon nanotube may be filtered 3 to 5 times through the surface of the fiber (110) by the vacuum adsorption method. In this case, most of the carbon nanotubes may remain on the surface of the fiber (110), and most of the carbon nanotubes remaining on the surface of the fiber (110) may be dried and deposited on the surface of the fiber (110).

Also, in order to form the carbon nanotube layer (130) by a vacuum adsorption method, the carbon nanotubes are required to remain on the surface thereof and only the dispersing medium (11) is required to pass. Thus, the fiber (110) may be appropriate for the use in the vacuum adsorption method, and in the present invention, the fiber (110) is used for the vacuum adsorption method. In addition, the fiber (110) may be utilized in a wearable device, and each fiber (110) has a grain with different properties. In this case, since the fiber (110) has different resistance displacement with respect to an elongated length along the grain, directional nature may be provided during the resistance displacement.

In the forming step of the carbon nanotube layer (S400), the functional group of the self-assembled monolayer and the hydroxyl group (—OH) of the carbon nanotube may make an ionic bond. The functional group in the functional group unit included in the self-assembled monolayer and the hydroxyl group of the carbon nanotube may make an ionic bond to form the carbon nanotube layer (130). For example, the hydroxyl group ($H^-$) formed on the surface of the carbon nanotube and the amine group ($NH^+$) of the functional group unit may make an ionic bond. Accordingly, the fiber (110) and the carbon nanotube layer (130) may be combined with even stronger energy, and thus, the bonding force between the fiber (110) and the carbon nanotube layer (130) may be increased, and the sensitivity and the durability of the wearable sensor may be improved.

Accordingly, the method for manufacturing the wearable sensor of the present invention is a vacuum adsorption method, and the carbon nanotube layer (130) is formed so that the carbon nanotubes may penetrate into the fiber (110) by a strong vacuum pressure. In addition, the hydroxyl group ($OH^-$) on the surface of the carbon nanotube and the functional group (for example, $NH^+$) of the self-assembled monolayer which is formed on the surface of the fiber (110) may make an ionic bond. Accordingly, the fiber (110) and the carbon nanotube layer (130) may be combined with even stronger energy. Thus, a wearable sensor may be manufactured as the fiber (110) on which the carbon nanotubes with even higher durability are adsorbed (or coated) by using a vacuum adsorption method.

Meanwhile, the fiber (110) absorbing moisture after filtering the carbon nanotubes may be dried. In this case, the drying may be performed at room temperature (about 21 to 25° C.) for 18 to 30 hours and then, at 30 to 50° C. for 30 minutes to 1 hour and 30 minutes, and complete drying may be performed at 70 to 90 C°.

The method for manufacturing the wearable sensor of the present invention may further include a forming step of a ductile protective layer which is coated on the carbon nanotube layer (130) (S500). The protective layer may be formed using a soft material and may be coated on the carbon nanotube layer (130). The carbon nanotube layer (130) may be exfoliated due to the excessive deformation (for example, frequent deformation, the deformation greater than the elasticity limitation of the carbon nanotube layer, etc.) or rapid deformation of the fiber (110). However, by coating the protective layer on the carbon nanotube layer (130), the ductile protective layer which may be retractile according to the deformation of the fiber (110), the exfoliation of the carbon nanotube layer (130) may be prevented, and the stress of the carbon nanotube layer (130) due to the surface area change according to the deformation of the fiber (110) may be relieved. The protective layer (140) may be formed using a resin, and any soft material having excellent elasticity to be retractile according to the deformation of the fiber (110), may be satisfied, without specific limitation.

For example, after vacuum adsorbing the carbon nanotubes on the fiber (110) by a vacuum adsorption method, the fiber (110) and the carbon nanotubes may be dried to form a carbon nanotube layer (130). Also, by applying a resin on the carbon nanotube layer (130) which is formed on the fiber (110), the ductile protective layer may be formed. Thus, the deformation of the carbon nanotube during the exfoliation of the carbon nanotube layer (130) and the deformation of the fiber (110) may be prevented by the protective layer.

Meanwhile, the method for manufacturing a wearable sensor of the present invention may further include a forming step of an electrode on the carbon nanotube layer (130). The electrode may be electrically connected with the carbon nanotube layer (130), and may be formed at both ends of the carbon nanotube layer (130). By flowing current through the carbon nanotube layer (130) via the electrode, the resistance displacement of the carbon nanotube layer (130) may be sensed. In addition, the electrode may be formed by sewing conductive threads such as silver (Ag) threads and gold (Au) threads. In this case, current may be uniformly supplied to entire carbon nanotube layer (130) without short circuit, and the current may be supplied to entire carbon nanotube layer (130). In addition, the electrode may be simply formed on the carbon nanotube layer (130), and the electrode may be formed without a separate etching process after forming a protective layer (140). In addition, if the fiber (110) and the carbon nanotube layer (130) are sewn using conductive threads, the electrode may be simply manufactured, and in addition, the fiber (110) and the carbon nanotube layer (130) may be firmly bonded (or fixed).

FIG. 6 is a schematic cross-sectional view showing the manufacturing process of a wearable sensor according to another embodiment of the present invention.

Referring to FIG. 6, in the forming step of the carbon nanotube layer (S400), the carbon nanotube layer may be continuously formed on the self-assembled monolayer while transporting the fiber (110) in a crossing direction to the supplying direction of the dispersion solution (13). By continuously vacuum adsorbing the carbon nanotubes on the self-assembled monolayer while transporting the fiber (110) in a crossing direction (for example, in a longitudinal direction of the fiber) to the supplying direction of the dispersion solution (13), the carbon nanotube layer (130) may be simply formed. The carbon nanotube layer (130) may be continuously formed on the fiber (110) while transporting the fiber (110). In this case, the carbon nanotube layer (130) may be formed on the fiber (110) (that is, on the self-assembled monolayer) by an in-line process while transporting the fiber (110). Meanwhile, the fiber (110) may be immersed in a surface treatment solution by transporting the fiber (110) using a transporting part (not shown) such as a conveyor belt. Here, by continuously transporting the fiber (110) immersed in the surface treatment solution via the transporting part (not shown), the fiber (110) may be provided at a position for forming the carbon nanotube layer (130). Accordingly, the fiber (110) on which the self-assembled monolayer is formed may be continuously provided, and only if the dispersion solution (13) of the carbon nanotubes is continuously supplied, all processes for manufacturing the wearable sensor may be performed through an in-line process.

Therefore, the process for manufacturing a wearable sensor while transporting the fiber (110) may be performed as an in-line process, and the mass production of the wearable sensor may be even more advanced.

As described above, in the present invention, the resistance displacement of the carbon nanotube layer may be sensed or measured according to the deformation of the fiber by providing carbon nanotubes on a fiber to form a carbon nanotube layer. Accordingly, the deformation of the fiber may be sensed by the resistance displacement of the carbon nanotube layer, the biotransformation of a wearer may be sensed by measuring the resistance displacement due to the deformation of the fiber, which may be changed according to the biotransformation of the wearer. In addition, a self-assembled monolayer including a functional group is formed on a fiber, a hydroxyl group (—OH) is formed on the surface of a carbon nanotube, and a carbon nanotube layer is formed on the self-assembled monolayer formed in the fiber, thereby improving the bonding force between the fiber and the carbon nanotube layer due to the ionic bond of the functional group and the hydroxyl group, increasing the sensitivity and durability of the wearable sensor. In addition, a ductile protective layer is coated on the carbon nanotube layer to prevent the exfoliation of the carbon nanotube layer. Meanwhile, in the present invention, a carbon nanotube layer is formed by vacuum adsorption, and the carbon nanotube layer is adsorbed well on the fiber and a processing time for forming the carbon nanotube layer may be decreased. In addition, since the carbon nanotube layer is formed by an in-line process while transporting the fiber, the mass production of the wearable sensor may be further advanced.

Although the preferred embodiments of the present invention have been described, it is understood that the present invention should not be limited to these embodiments but various changes and equivalent other embodiments can be made by one ordinary skilled in the art without deviating from the gist of the present invention within the scope of the present invention as hereinafter claimed. Thus, the scope of the technical protection of the present invention is to be determined by the following claims.

What is claimed is:

1. A wearable sensor, comprising:
   a fiber;
   a self-assembled monolayer including a functional group and being formed on at least one surface of the fiber;
   a carbon nanotube layer formed on the self-assembled monolayer by adsorbing a plurality of carbon nanotubes on the self-assembled monolayer; and
   an electrode electrically connected to the carbon nanotube layer,
   wherein a hydroxyl group (—OH) is formed on the surface of the carbon nanotube, and
   wherein the hydroxyl group (—OH) of the carbon nanotube and the functional group of the self-assembled monolayer make an ionic bond.

2. The wearable sensor according to claim 1, further comprising a ductile protective layer which is coated on the carbon nanotube layer.

3. The wearable sensor according to claim 1, wherein the self-assembled monolayer comprises:
   a root unit combined with the at least one surface of the fiber; and
   a functional group unit comprising the functional group and being connected with the root unit.

4. The wearable sensor according to claim 1, wherein the functional group is at least one selected from the group consisting of an amine group (—NH), an amino group (—NH2), a thiol group (—SH), a carboxyl group (—COOH), a formyl group (—CHO), a cyanato group (—OCN), a silanol group (Si—OH), a phosphine group (—PO2H2), a phosphone group (—PO3H2), a sulfone group (—SO3H), and an epoxy group.

5. The wearable sensor according to claim 1, wherein the fiber is formed using an elastic material.

6. The wearable sensor according to claim 1, wherein the wearable sensor senses a resistance change of the carbon nanotube layer according to a deformation of the fiber.

7. A method for manufacturing a wearable sensor, the method comprising:
   forming a self-assembled monolayer comprising a functional group on a fiber;
   acid treating carbon nanotubes;
   dispersing the carbon nanotubes in a dispersing medium; and
   forming a carbon nanotube layer on the self-assembled monolayer by providing on at least one surface of the fiber a dispersion solution in which the carbon nanotubes are dispersed in the dispersing medium,
   wherein, in the acid treating the carbon nanotubes, at least a portion of carbon bonds is removed from the surface of the carbon nanotubes,
   the method further comprises forming a hydroxyl group (—OH) on the at least one surface of the carbon nanotube from which the carbon bond is removed.

8. The method for manufacturing a wearable sensor according to claim 7, wherein, in the forming the carbon nanotube layer, the carbon nanotubes are vacuum-adsorbed on the self-assembled monolayer while filtering the dispersion solution, by forming a vacuum pressure on another surface of the fiber.

9. The method for manufacturing a wearable sensor according to claim 7, wherein, in the forming the self-assembled monolayer, the fiber is immersed in a surface treatment solution comprising the functional group, for forming the self-assembled monolayer on the at least one surface of the fiber.

10. The method for manufacturing a wearable sensor according to claim 7, further comprising forming a ductile protective layer which is coated on the carbon nanotube layer.

11. The method for manufacturing a wearable sensor according to claim 7, wherein, in the forming the carbon nanotube layer, the carbon nanotube layer is continuously formed on the self-assembled monolayer while transporting the fiber in a crossing direction to the providing direction of the dispersion solution.

12. The method for manufacturing a wearable sensor according to claim 7, wherein, in the forming the carbon nanotube layer, the functional group of the self-assembled monolayer and the hydroxyl group (—OH) of the carbon nanotube make an ionic bond.

* * * * *